United States Patent [19]

Lazaroff

[11] Patent Number: 5,112,742
[45] Date of Patent: May 12, 1992

[54] SCREENING FOR ANTI-ADHESIN ANTIBIOTICS BY EMPLOYING PHOTOINDUCED CYANOBACTERIA

[75] Inventor: Norman Lazaroff, Vestal, N.Y.

[73] Assignee: State University of New York, Albany, N.Y.

[21] Appl. No.: 484,212

[22] Filed: Feb. 23, 1990

[51] Int. Cl.$^5$ .................. C12Q 1/18; C12P 17/08; C07D 321/04

[52] U.S. Cl. ................... 435/32; 435/124; 549/267

[58] Field of Search ............... 435/32, 124; 549/267

[56] References Cited

PUBLICATIONS

N. Lazaroff, "Chemical inhibition of harmogonial motility and aggregation in a nitrogen fixing cyanobacterium" *Abst. First Int. Phycological Congress*, St. Johns, Newfoundland (1982).
N. Lazaroff, E. DiBlasio, & C. Tannenbaum, "A comparative study of photoinduced nostocacean development" *Abst. Phycol. Soc. Meeting* 1984, Ft. Collins, Colo. p. 23.
N. Lazaroff, "Hotomorphogenesis and nostocacean development" pp. 279-319, *The Biology of Blue-Green Algae*, Blackwell Scientific, Oxford 1973.
N. Lazaroff, "Experimental control of nostocacean development" *Symposium on Taxonomy and Biology of Blue-green algae*, Madras University Press, pp. 521-544 (1972).
N. Lazaroff, "Control of hormogonial release and motility in a filamentous blue-green algae" Abst. of XI Int. Botan. Cong., Seattle 1969 p. 123.
N. Lazaroff & P. M. Jackson, "Hormogonial aggregation and colonial morphogenesis of Nostoc Muscorum" Abst. A.S.L.O. & Phycol. Soc. p. 73, (1986).
N. Lazaroff & W. Vishniac, "The effect of light on the development cycle of *Nostoc muscorum A* filamentous blue-green algae" *Journal General Microbiology* 25 pp. 365-374 (1961).

Primary Examiner—Robert A. Wax
Assistant Examiner—Bradley L. Sisson
Attorney, Agent, or Firm—Morgan & Finnegan

[57] ABSTRACT

The present invention relates to the method of screening for antibiotics employing a cyanobacterium, *Nostoc muscorum A*. The cyanobacterium is photoinduced under specified growing conditions to enable the cyanobacterium to be employed for screening of chemicals or organisms that exhibit anti-adhesin properties. These anti-adhesin properties are characterized by zones of interference in the photoinduced lawns of the cyanobacterium.

11 Claims, 3 Drawing Sheets

A) INTERFERENCE WITH SPIRAL AGGREGATION ON PHOTOINDUCED LAWN.
B) TRICHOME DESTRUCTION; CLEARING OF AGAR LAYER ON PHOTOINDUCED OR UN-INDUCED LAWN.
C) DOUBLE ZONES; INHIBITION OF AGGREGATION AND DESTRUCTION OF CYANOBACTERIAL TRICHOMES IN PHOTOINDUCED LAWN.
D) PHOTOINDUCED SPIRAL AGGREGATION OF HORMOGONIA.
E) UN-INDUCED LAWN OF HETEROCYSTOUS FILAMENTS.

A) INTERFERENCE WITH SPIRAL AGGREGATION ON PHOTOINDUCED LAWN.

B) TRICHOME DESTRUCTION; CLEARING OF AGAR LAYER ON PHOTOINDUCED OR UN-INDUCED LAWN.

C) DOUBLE ZONES; INHIBITION OF AGGREGATION AND DESTRUCTION OF CYANOBACTERIAL TRICHOMES IN PHOTOINDUCED LAWN.

D) PHOTOINDUCED SPIRAL AGGREGATION OF HORMOGONIA.

E) UN-INDUCED LAWN OF HETEROCYSTOUS FILAMENTS.

SCREENING FOR ANTI-ADHESIN ANTIBIOTICS BY EMPLOYING PHOTOINDUCED CYANOBACTERIA

INTRODUCTION

The present invention is directed to a method of screening for antibiotics. In particular, the present invention is directed to a method of using a cyanobacterium, *Nostoc muscorum A*, to screen chemicals or source of organisms for anti-adhesin properties for use as an antibiotic.

BACKGROUND OF THE INVENTION

*Nostoc muscorum A* is a species of cyanobacterium (blue green alga) whose life cycle has been extensively studied. The normal life cycle of the *Nostoc muscorum A* can be described as having the following stages which are illustrated in FIG. 1.

Stage 1 consists of the hormogone or motile trichome (mt) with tapered terminal cells (tc). In stage 2, the terminal cells begin differentiation to terminal heterocysts (th) and the intercalary cells enlarge. In stages 3 and 4, the intercalary cells continue to enlarge and form clusters while a gelatinous sheath forms around each of the clusters. In stage 5, the cells in each of the enclosed clusters align to form filaments (f). In stage 6, the newly formed filaments begin to form intercalary heterocysts (ih) (heterocystous filaments). In stage 7, the gelatinous sheath begins to break down. In stage 8, the filaments break at the intercalary heterocysts giving rise to hormogonia and heterocysts. In stage 9, the swarming (gliding) hormogonia may form spiral aggregates (sa) of the motile elements (called motile trichomes). When these stop moving, the life cycle then can repeat.

This life cycle can be affected by light and by growth medium composition. When *Nostoc muscorum A* is grown heterotrophically, in complete darkness, in a growth medium containing the sugars glucose or sucrose, the Nostoc strain grows in a coccoid form called the aseriate stage, which upon exposure to light differentiates synchronously to the filamentous stage. The filaments break, release their heterocysts and then further differentiate to form hormogonia.

However, if the growth culture contains glucose and the growth culture is incubated under cool-white fluorescent illumination, then the formation of hormogonia becomes progressively inhibited. As a result, the mature culture with glucose consists exclusively of long unbroken heterocystous filaments. The wooly appearance of this type of growth in culture is termed "lanose".

Additionally, if the lanose culture, grown in continuously shaken glucose-containing media under cool-white fluorescent light, is then exposed to red fluorescent light, the heterocystous filaments convert to motile hormogonia. Subsequently, if the hormogonial suspension is placed in unshaken vessels in cool-white fluorescent light, these hormogonia swarm on surfaces or in semi-solid media to form tight spiral aggregates of gliding motile trichomes. In addition, the liberation of the hormogonia produces free heterocysts, which display a high frequency of germination, if produced after growing in a culture containing Medium I and approximately $10^{-3}$% proteose peptone in addition to glucose.

Plating out germinable heterocysts and picking individual microcolonies derived from single heterocysts allow for the routine isolation of various strains of Nostoc muscorum A which differ in their properties of hormogonial motility and aggregation.

Further, the mechanisms of red light induction and photo-reversal are non-photosynthetic. Very small amounts of light energy are required to induce filamentous development of the aseriate cells. Development occurs in darkness following short light exposures. Red-light quanta from the 650 nm region of the spectrum induce development and green-light quanta, approx. 500-590 nm, reverse the effects of red light exposure.

It has been further shown that the hormogonial aggregation is accomplished by the formation of sticky protuberant strands of mucilaginous material that hold the motile hormogonia together. Based on the specificity of substances that inhibit aggregation and observation by electron microscopy of the attachment fibers, it is believed that aggregation is dependent upon the synthesis of adhesins, consisting of externally secreted proteins, probably glycoproteins.

Moreover, microbiologists have come to believe that free-living and/or parasitic bacteria frequently attack a cell or organism by an initial attachment to that cell or organism. Therefore, it would be beneficial to prevent such attack by developing a new class of antibiotics which counteract the synthesis of bacterial adhesins responsible for the localization of bacterial pathogens at specific infection (attachment) sites. It is also believed that by blocking bacterial attachment to host cells/organisms the unattached bacteria are rendered more susceptible to the natural immune defenses of the body and to chemotherapeutic and/or prophylactic drug treatment.

Generally speaking, conventional screening methods for antibiotics focus on finding chemicals that are lethal or growth-inhibiting in action against the disease-causing organism. These screening methods employ techniques that detect the effectiveness of a chemical's action in affecting growth and viability of test organisms by mechanisms that include interference with cell wall formation, destruction of cellular membranes, and inhibition of biosynthesis or nutrient uptake. Therefore, conventional screening methods dependent upon inhibition of growth and viability are in that respect limited to the kinds of antibiotic producers that can be identified.

LIST OF REFERENCES

The following references relate generally to the subject area.

1. N. Lazaroff. "Control of hormogonial release and motility in a filamentous blue-green alga" *Abst. of XI Int. Botan. Cong., Seattle* 1969 p. 123.
2. N. Lazaroff. "Chemical inhibition of hormogonial motility and aggregation in a nitrogen fixing cyanobacterium" *Abst. First Int. Phycological Congress*, St. Johns, Newfoundland (1982).
3. N. Lazaroff, E. DiBlasio, & C. Tannenbaum. "A comparative study of photoinduced nostocacean development" *Abst. Phycol. Soc. Meeting* 1984, Ft. Collins, CO. p. 23.
4. N. Lazaroff & P. M. Jackson. "Hormogonial aggregation and colonial morphogenesis of *Nostoc Muscorum*" *Abst. A.S.L.O. & Phycol. Soc.* p. 73. (1986).
5. N. Lazaroff. "Photomorphogenesis and nostocacean development" p. 279-319, *The Biology of Blue-Green Algae*, Blackwell Scientific, Oxford 1973.
6. N. Lazaroff & W. Vishniac. "The effect of light on the development cycle of *Nostoc muscorum A* filamentous blue-green algae" *Journal General Microbiology* 25 p. 365-374 (1961).
7. N. Lazaroff. "Experimental control of nostocacean development" *Symposium on Taxonomy and Biology of Blue-green algae.* Madras University Press, p. 521-544 (1972).

SUMMARY OF THE INVENTION

Accordingly, it is an object of this invention to develop a novel screening method for identifying a new class of antibiotics, which can be called anti-adhesin antibiotics. These anti-adhesin antibiotics have the advantage of only preventing the bacterial attachment and of not killing or interfering with the growth of the cell.

It is another object of this invention to provide a novel screening method that is comparatively rapid and inexpensive.

It is yet another object of this invention to provide a novel screening method that does not kill or inhibit the growth of the test organism.

It is yet another object of this invention to provide a novel screening method that determines the relative potency of the anti-adhesin antibiotic.

It is yet another object of this invention to provide a novel screening method that characterizes as displaying anti-adhesin properties a specific chemical in solution or a specific organism in a mixture of organisms or a mixed suspension of organisms.

The present invention provides a novel photobiological screening method for identifying sources of anti-adhesin antibiotics comprising the steps of:

A. seeding a Nostoc layer;

B. illuminating the seeded Nostoc layer with light deficient in the red portion of the spectrum;

C. pouring a top growth medium over the illuminated seeded Nostoc layer to form a two-layer system;

D. solidifying the two-layer system and placing chemicals or source of organisms, that will be screened for anti-adhesin properties, on the solidified two-layer system to form a test system;

E. incubating the test system while simultaneously illuminating the test system under light deficient in the red portion of the spectrum in order to grow heterocystous filaments in the seeded Nostoc layer;

F. incubating the illuminated test system under red fluorescent light;

G. observing in the seeded Nostoc layer the photoinduced lawns and zones of interference with hormogonial motility and aggregation; and H. characterizing, at the specific sites of interference with hormogonial activity, specific organisms in the source of organisms or a specific chemical as displaying anti-adhesin antibiotic properties.

DETAILED DESCRIPTION OF THE INVENTION

Figure 1:
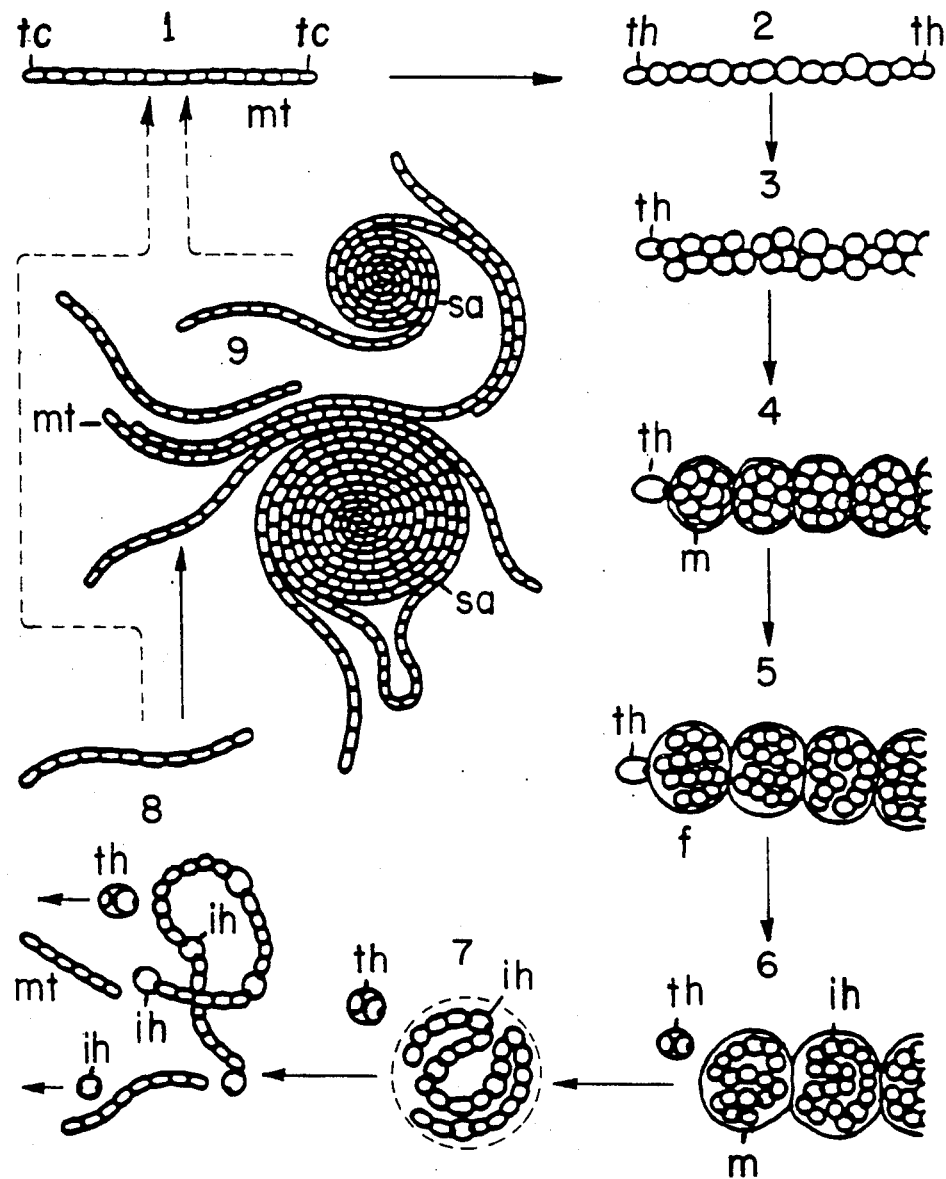
FIG. 1 is a drawing of the normal development cycle of *Nostoc muscorum A* in culture showing stages 1 to 9.

The process of the present invention for screening for anti-adhesin antibiotics by employing photoinduced cyanobacteria comprises the steps of:

A. preparing a seeded Nostoc layer which involves growing an axenic Nostoc strain under cool-white fluorescent light for about 7-14 days to develop heterocystous filaments, sedimenting the heterocystous filaments, washing and re-suspending the sedimented heterocystous filaments, adding the re-suspended filaments to a molten bottom growth layer at about 42°-45° C., pouring the composition of filaments and molten bottom growth layer into a container and solidifying the container;

B. illuminating the seeded Nostoc layer under cool-white fluorescent light for about 48-72 hours at about 20°-24° C.;

C. Pouring a top growth medium at about 40°-45° C. over the illuminated seeded Nostoc layer to form a two-layer system;

D. solidifying the two-layer system;

E. placing chemicals or source of organisms (that will be screened for anti-adhesin properties) on the solidified two-layer system to form a test system;

F. incubating the test system for about 48-72 hours at about 20°-27° C. while simultaneously illuminating the test system under cool-white fluorescent light in order to grow heterocystous filaments in the seeded Nostoc layer;

G. incubating the test system under red fluorescent light for about 24-48 hours at about 20°-25° C. to produce a reticular pattern of swarming and aggregation in the seeded Nostoc layer; and H. observing in the seeded Nostoc layer the photoinduced lawns and determining the presence of zones of interference to the background reticular pattern of swarming and aggregation (the formation of the zones of interference indicates that anti-adhesin properties of the organisms or chemicals are present).

The individual stages of the present invention are described in detail below.

Seeded Nostoc layer

The Nostoc strain that is found to give the best results is the h-3 clone of *Nostoc muscorum A.* Other strains that may be used include h-1 and h-2 clones of *Nostoc muscorum A* as well as the original parent strain of *Nostoc muscorum A.* The h-3 clone was derived by germination of a single heterocyst of the parent strain. [parent strain-=UTEX #1037] As well, the substrain h-3 has been deposited at the American Type Culture Collection, Rockville, MD on Oct. 3, 1991, with deposit number 55240.

The bottom growth layer consists of Medium I plus about 0.9% purified agar, about 0.5-1.0% glucose and about $10^{-3}\%$ proteose peptone. The composition of Medium I per liter consists of 0.15 g $K_2HPO_4$, 0.20 g $MgSO_4\ 7H_2O$, 0.025 g $CaCl_2\ 2H_2O$, 0.025 g $Na_2SiO_3$, 2.0 mg $FeCl_3\ 6H_2O$, 0.4 mg $Na_2MoO_4\ 2H_2O$, 0.6 mg $H_3BO_3$, 0.04 mg $CuSO_4\ 5H_2O$, 0.04 mg $ZnSO_4\ 7H_2O$, and 1000 ml $H_2O$. The bottom growth layer may also contain 0.01 M pH 7.5 tricine buffer.

The seeded Nostoc layer is prepared by growing in a shaken culture for about 7-10 days the Nostoc strain under cool-white fluorescent light, using a growth medium of Medium I plus about 1% glucose and about $10^{-3}\%$ proteose tone. About 5 gms. of the Nostoc strain is recovered from the growth medium by centrifuging for about 15 minutes and washing once in Medium I. Subsequently, this washed Nostoc strain, filament suspension, may be used without further modifications or blended for about 30 seconds. The blended or long filamentous material is seeded in about 100 mls. of the molten bottom growth layer at 42° C.

About 10-12 mls. of the seeded Nostoc layer is either poured into a petri dish or on a previously formed feeder layer consisting of Medium I. The seeded Nostoc layer is allowed to solidify.

Light deficient in the red portion of the spectrum

The illumination level required is about 2-4 mW/cm$^2$. A cool white fluorescent light may be used.

Top growth medium

The top growth medium consists of about 5-10 mls of Medium I plus about 1.5% purified agar, about 0.5-1% sucrose, $10^{-3}\%$ proteose peptone and other additives if needed to produce a nutrient substrate for growth of the sources of organisms.

The top growth medium is poured over the seeded Nostoc layer at about 42°-43° C. to form a two-layer system. The two-layer system is solidified at room temperature. This solidified two-layer system is designed to separate the chemicals or source of organisms from the Nostoc strain.

Chemicals or Source of Organisms

About 0.1 ml of source of organisms is spread uniformly over the two-layer system to form a test system. The source of organisms may consist of pure or mixed cultures of organisms, or soil or water suspensions containing organisms.

Alternatively, the test system may consist of pure chemicals, mixtures or chemical solutions absorbed in other materials and placed on the two-layer system.

Incubation

The test system incubation is carried out for about 48-72 hours at about 22°-27° C. under illumination by cool-white fluorescent light. During the time when the Nostoc strain is forming heterocystous filaments in the seeded Nostoc layer, actinomycete, other bacterial colonies or other microbial growth forms on the top growth medium agar layer. At the same time, in order to continue to be screened as displaying anti-adhesin properties, the chemicals or source of organisms must produce little or no effect directly below in the seeded Nostoc layer which will have completed active growth in the form of heterocystous filaments.

In contrast, if destruction or clearing of the seeded lawn occurs (see FIG. 2B) then the chemicals or source of organisms directly above this destruction or clearing site will not be characterized as specifically displaying anti-adhesin properties.

Red fluorescent light

The test system is then exposed to red fluorescent light of about 0.5-1.0 mW/cm$^2$ for 24-48 hours at about 22° C. At the end of this phase, the filaments differentiate to form hormogonia and the hormogonia begin to swarm within the agar.

Antibiotic screening

Figure 2A:
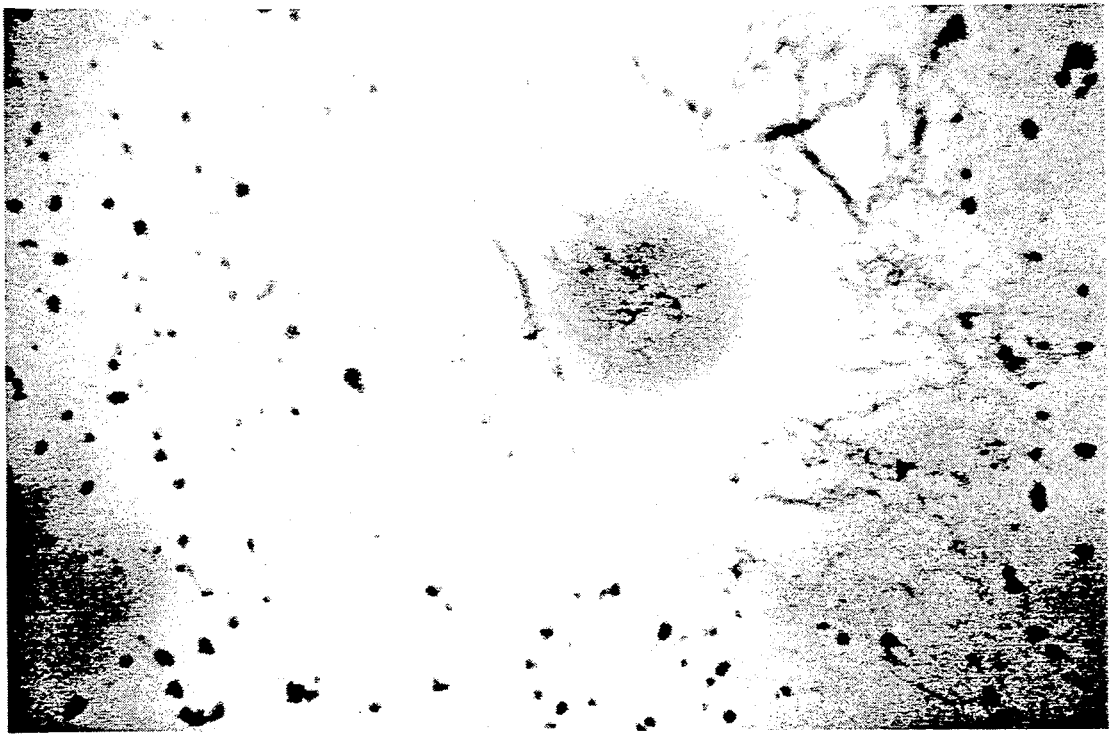
FIG. 2A is a photograph, under the microscope at about 4x magnification, of the zones of interference which occur when agar lawns of cool-white fluorescent illuminated glucose-grown heterocystous filaments, induced to develop by fluorescent lights, are interfered with by the inoculum.
Figure 2B:
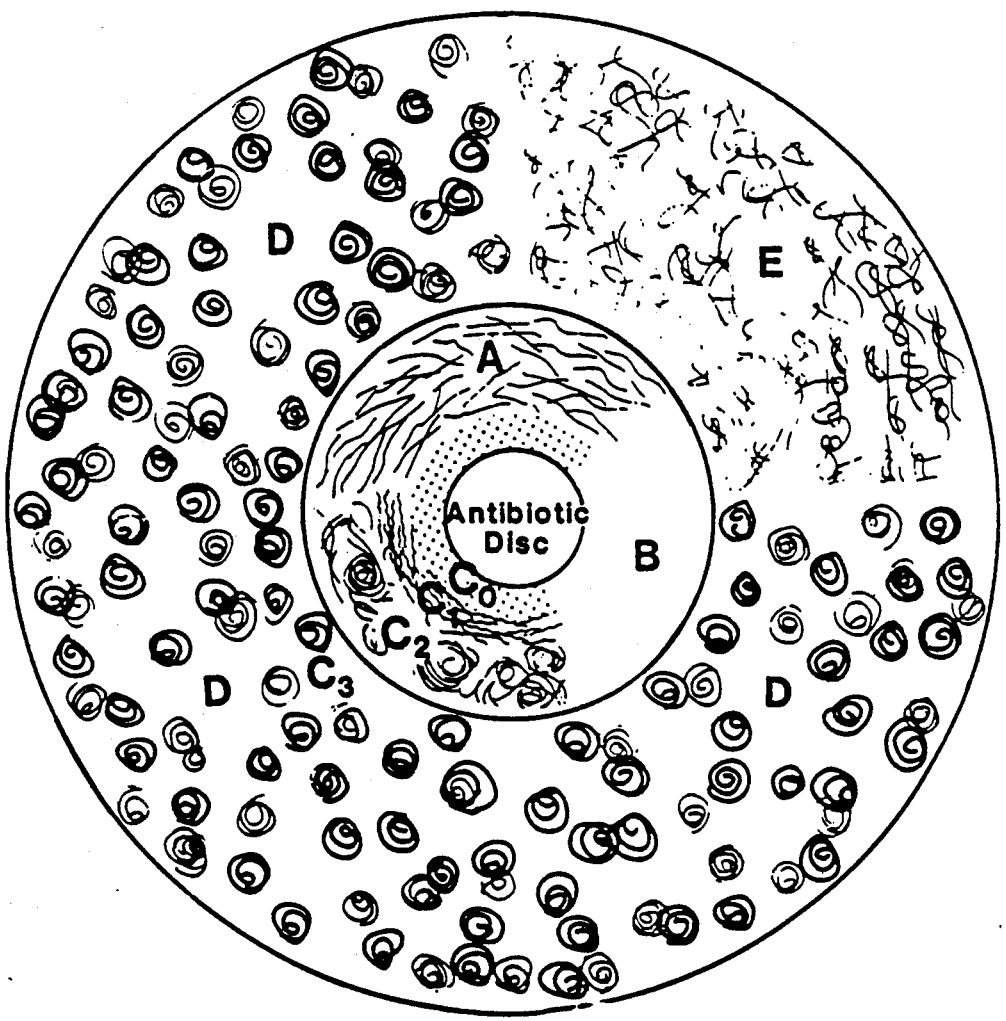
FIG. 2B is a composite drawing illustrating different effects of antibiotics on agar lawns seeded with *Nostoc muscorum A.*

If the reticular pattern of swarming aggregation in the lawn is interfered with but not killed (shown by clearing or destruction, FIG. 2B), then the chemicals or source of organisms are characterized as having anti-adhesin antibiotic properties (FIG. 2A). This interference is caused by anti-adhesin antibiotic substances either initially present in or formed from the source that diffused from the top growth medium directly over the seeded Nostoc lawn. Demonstration of this interference is indicative of a new class of antibiotics, anti-adhesin antibiotics. If the test system involved application of chemicals to the top layer then the specific chemical over the site of interference is categorized as an anti-adhesin antibiotic.

Alternatively, if the test system consisted of source of organisms then the specific organism over the site of interference is categorized as displaying anti-adhesin properties. This specific organism can be transferred to a suitable medium for propagation to produce particular anti-adhesin substances.

This novel screening method allows for exploitation of an entirely new physiological class of antibiotics, anti-adhesin antibiotics. This new class of antibiotics would prevent attachment of bacterial pathogens to particular receptors on the host cells' membranes. Such new antibiotics would cause little interference with normal host function since they would act on formation of substances specifically produced by bacteria. Simultaneously, the bacteria would survive and continue to grow, but would be more susceptible to elimination by host defenses. Counteraction of infection by such means would be less likely to result in selection for drug resistance because the anti-adhesin antibiotics involved need not favor the growth of mutants that are resistant to their action (do not affect growth).

EXAMPLE 1

Erlenmeyer flasks containing 100 mls. of shaken culture were used to propagate the h-3 clone of the Nostoc muscorum A strain. The flasks were incubated for 10 days under cool-white fluorescent light in shaken Nostoc cultures grown on Medium I plus 1% glucose and $10^{-3}\%$ proteose peptone. About 5 gm. of heterocystous filaments of the Nostoc strain were recovered aseptically by decanting, centrifuging, then washing once in Medium I. The filament suspension was neutralized to pH 7.2 with sterile 0.1 M tricine buffer. The strain was blended for 30 seconds in a sterile Waring Microblendor.

A bottom growth layer was prepared by mixing Medium I, 0.9% purified agar, 0.5% glucose and $10^{-3}\%$ proteose peptone at a temperature high enough to liquify the mixture.

The strain was then added to 100 mls. of the molten bottom growth layer at 42° C. Approximately 12 ml. of this seeded liquid agar medium was poured into each petri dish to solidify a seeded Nostoc layer.

The solidified seeded Nostoc layer was illuminated under cool-white fluorescent light, approximately 2 mW/cm$^2$, for 48 hours at 22° C.

A top growth medium was prepared by mixing 10 mls. of Medium I plus 1.5% purified agar, 1% sucrose and $10^{-3}\%$ proteose peptone. The top growth medium was poured over the illuminated seeded Nostoc layer at 42° C. to produce a two-layer system. The two-layer system was allowed to solidify at room temperature.

The sources of organisms was spread across the solidified top growth medium to form a test system. The test system was then incubated for approximately 1 week at 22°-27° C. while illuminated under cool-white fluorescent light, 2 mW/cm$^2$.

The test system was then exposed to red fluorescent light, 1 mW/cm$^2$, for 24-48 hours. Subsequently, a zone of interference to the reticular pattern of aggregation in the lawn was observed in the seeded Nostoc layer. This site of interference was caused by a substance produced by an organism from the source growing directly above on the top growth medium. A colony of organisms at the site of this interference was identified as displaying anti-adhesin antibiotic properties (See FIG. 2A: for zones of interference). This interference was caused by the organism on the top growth medium producing an anti-adhesin antibiotic, i.e. soluble substance that diffused into the seeded Nostoc layer and affected aggregation of the hormogonia.

This organism was picked from the appropriate colony on the top growth medium by a sterile needle. Then, the organism was transferred to a liquid culture medium for propagation and recovery of the anti-adhesin antibiotic.

EXAMPLE 2

In this example, the relative potency of a test anti-adhesin chemical is screened.

Erlenmeyer flasks containing 100 mls. of shaken culture are used to propagate the h-3 clone of the Nostoc muscorum A strain. The flasks are incubated for 10 days under cool-white fluorescent light to produce shaken Nostoc cultures grown on Medium I plus 1% glucose and $10^{-3}$% proteose peptone. The heterocystous filaments of about 5 gms. of the Nostoc strain are recovered aseptically by decanting, centrifuging, then washing once in Medium I. The filament suspension is neutralized to pH 7.2 with sterile 0.1 M tricine buffer. The strain is blended for 30 seconds in a sterile Waring Microblendor.

A bottom growth layer is prepared by mixing Medium I, 0.9% purified agar, 0.5% glucose and $10^{-3}$% proteose peptone.

The strain is then added to 100 mls. of the molten bottom growth layer at 42° C. Approximately 12 ml. of the liquid seeded Nostoc layer is poured into each petri dish to produce a seeded Nostoc layer.

The seeded Nostoc layer is illuminated under cool-white fluorescent light, approximately 2 mW/cm$^2$, for about 72-96 hours at 22° C.

The chemical to be tested is produced by growing a testing organism in a suitable media in order to produce the anti-adhesin substance. Then, the test organism is removed from the media. Subsequently, the remaining solution of media and anti-adhesin substance is concentrated to the degree desired in order to test the concentrates' relative potency. The resulting concentrated media and anti-adhesin substance is taken up in a porous filter paper disc or an agar block to form the test chemical block.

The test chemical block is placed on the seeded Nostoc layer to form the test system. The test system is then incubated for approximately 24 hours at 22°-27° C. while illuminated under cool-white fluorescent light, 2 mw/cm$^2$.

The test system is then exposed to red fluorescent light, 1 mw/cm$^2$, for 24-48 hours. Subsequently, a zone of interference to the reticular pattern of aggregation in the lawn is observed in the seeded Nostoc layer surrounding the test chemical block. This chemical producing the specific site of interference is identified as an anti-adhesin antibiotic.

This test is further repeated with a dilution in concentration of the anti-adhesin substance in the test chemical block until no zone of interference is observed. The dilution required to alter the diameter of the measured zone of interference relative to the control determines the relative potency of the test chemical.

What is claimed is:

1. A method for screening chemicals or source of organisms to determine whether a chemical or source of organisms interferes with spiral aggregation in a Nostoc lawn comprising:
   A. preparing a seeded Nostoc layer by growing a Nostoc strain in light deficient in the red portion of the spectrum for about 7-14 days, sedimenting said growth strain, washing said sedimented strain and adding said washed strain to a bottom growth layer containing Medium I plus about 0.7-0.9% purified agar, about 0.5-1.0% glucose and about $10^{-3}$% proteose peptone;
   B. illuminating said seeded Nostoc layer under light deficient in the red portion of the spectrum for about 48-72 hours at about 22°-25° C.;
   C. pouring a top growth medium containing Medium I plus about 0.5-1.0% sucrose, about $10^{-3}$% proteose peptone and about 1.0-1.5% purified agar over said illuminated seeded Nostoc layer to form a two-layer system;
   D. solidifying said two-layer system;
   E. placing on said solidified two-layer system chemicals or a source of organisms to form a test system;
   F. incubating said test system for about 48-72 hours at about 20°-27° C. while simultaneously illuminating said test system under light deficient in the red portion of the spectrum;
   G. incubating said illuminated test system under red fluorescent light for about 24-48 hours; and
   H. observing zone of interference formed from the presence of said chemicals or source of organisms in the lawn of aggregating hormogonia produced from the seeded Nostoc layer.

2. A method described in claim 1, wherein said Nostoc strain is selected from the group consisting of h-3 clone of *Nostoc muscorum A;* h-1 clone of *Nostoc muscorum A* and h-2 clone of *Nostoc muscorum A.*

3. A method described in claim 1 wherein said Nostoc strain is neutralized to a pH of about 7.2 prior to illuminating with said light deficient in the red portion of the spectrum.

4. A method described in claim 1 wherein said Medium I contains about 0.15 g K$_2$HPO$_4$, 0.20 g MgSO$_4$.7H$_2$O, 0.025 g CaCl$_2$, 2H$_2$O, 0.025 g Na$_2$SiO$_3$, 2.0 mg FeCl$_3$ 6H$_2$O, 0.4 mg Na$_2$MoO$_4$.2H$_2$O, 0.6 mg H$_3$BO$_3$, 0.04 mg CuSO$_4$.5H$_2$O, 0.04 mg ZnSO$_4$.7H$_2$O, and 1000 ml H$_2$O.

5. A method described in claim 1 wherein said light deficient in the red portion of the spectrum is a cool-white fluorescent light.

6. A method described in claim 1 wherein said bottom growth layer is formed by seeding blended homogenized fragments of trichomes in agar media containing 1% glucose and 0.001% proteose peptone.

7. A method described in claim 1 wherein said source of organisms comprises pure cultures, mixed cultures, soil suspensions or water suspensions.

8. A method described in claim 1 wherein said chemicals comprises pure chemicals, chemical solutions, or solution concentrated for determination of relative potency.

9. A method described in claim 1 further comprising:
I. identifying colonies of said source of organisms at the zones of interference; and
J. transferring said colonies to a suitable medium for propagation to produce substances.

10. A method for screening chemicals or source of organisms to determine whether a chemical or source of organisms interferes with spiral aggregation in a Nostoc lawn comprising:
A. preparing a seeded Nostoc layer by growing a Nostoc strain in light deficient in the red portion of the spectrum for about 7-14 days, sedimenting said growth strain, washing said sedimented strain and adding said washed strain to a bottom growth layer containing Medium I plus about 0.7-0.9% purified agar, about 0.5-1.0% glucose and about 10-3% proteose peptone;
B. illuminating said seeded Nostoc layer under light deficient in the red portion of the spectrum for about 48-72 hours at about 22°-25° C.;
C. solidifying said seeded illuminated Nostoc layer;
D. placing on said solidified seeded Nostoc layer a chemical to form a test system;
E. incubating said test system for about 24 hours at about 20°-27° C. while simultaneously illuminating said test system under light deficient in the red portion of the spectrum;
F. incubating said illuminated test system under red fluorescent light for about 24-48 hours; and
G. observing zones of interference formed from the presence of said chemical in the lawns of aggregating hormogonia produced from the seeded Nostoc layer.

11. A method described in claim 10 wherein said chemical comprises pure chemicals, chemical solutions or solution concentrated for determination of relative potency.

* * * * *